US007929741B2

(12) United States Patent
Guiliguian et al.

(10) Patent No.: US 7,929,741 B2
(45) Date of Patent: Apr. 19, 2011

(54) SYSTEM AND METHOD FOR AUTOMATED DETECTION OF MUCUS PLUGS WITHIN BRONCHIAL TREE IN MSCT IMAGES

(75) Inventors: Diran Guiliguian, Paris (FR); Benjamin Odry, West New York, NJ (US); Atilla Peter Kiraly, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 839 days.

(21) Appl. No.: 11/836,966

(22) Filed: Aug. 10, 2007

(65) Prior Publication Data

US 2008/0101675 A1 May 1, 2008

Related U.S. Application Data

(60) Provisional application No. 60/822,285, filed on Aug. 14, 2006.

(51) Int. Cl.
G06K 9/00 (2006.01)
(52) U.S. Cl. ..................................... 382/128
(58) Field of Classification Search .................. 382/128, 382/130–132; 128/922; 378/4, 21; 600/410, 600/425
See application file for complete search history.

(56) References Cited

U.S. PATENT DOCUMENTS

| 6,694,163 | B1 * | 2/2004 | Vining | 600/407 |
| 7,194,117 | B2 * | 3/2007 | Kaufman et al. | 382/128 |
| 7,574,024 | B2 * | 8/2009 | Bitter et al. | 382/128 |
| 7,715,608 | B2 * | 5/2010 | Vaz et al. | 382/131 |
| 7,822,461 | B2 * | 10/2010 | Geiger et al. | 600/415 |
| 2004/0267114 | A1 * | 12/2004 | Mundy et al. | 600/427 |
| 2005/0182295 | A1 * | 8/2005 | Soper et al. | 600/117 |

* cited by examiner

Primary Examiner — Matthew C Bella
Assistant Examiner — Shervin Nakhjavan

(57) ABSTRACT

A method for detecting and localizing mucus plugs in digitized lung images, includes providing a digitized lung image volume comprising a plurality of intensities corresponding to a 3-dimensional grid of points, extracting a bronchial tree from said lung image, said bronchial tree comprising a plurality of branching airways terminating at terminal points, providing a model of a 2-dimensional cross section of an airway, selecting an extended point beyond a terminal point of an airway branch in a direction of said airway branch, obtaining a 2-dimensional cross section I of size m×n points from said lung image about said selected point, processing said 2D cross section I by calculating a local neighborhood function for each point in the cross section and forming a union of all local neighborhood functions, and calculating a correlation between processed 2D cross section and said airway model, wherein said correlation is indicative of the presence of a mucus plug within said airway.

28 Claims, 7 Drawing Sheets ium of the invention as described
SYSTEM AND METHOD FOR AUTOMATED DETECTION OF MUCUS PLUGS WITHIN BRONCHIAL TREE IN MSCT IMAGES

CROSS REFERENCE TO RELATED UNITED STATES APPLICATIONS

This application claims priority from "Automated Detection of Mucus Plugs within Bronchial Tree in MSCT images", U.S. Provisional Application No. 60/822,285 of Guiliguian, et al., filed Aug. 14, 2006, the contents of which are herein incorporated by reference.

TECHNICAL FIELD

This disclosure is directed to the detection and location of mucus plugs that obstruct the airway tree.

DISCUSSION OF THE RELATED ART

Lung diseases characterized by chronic airway inflammation with resulting bronchiectasis, as frequently occurs in patients with atypical mycobacterial infections or cystic fibrosis, among others, typically result in retained secretions. Extra mucus tends to pool in the airways, resulting in foci of mucoid impaction, causing further limitation or obstruction of air flow. Retained secretions also increase the risk of secondary airway infection. Mucus plugging frequently affects airflow, which can be severely restricted when extensive. Accurate assessment of the true extent and severity of disease optimally requires that all foci of mucoid obstruction be identified—even when airways peripheral to more centrally obstructed airways are involved. Unfortunately, to date, most attempts to characterize the extent and severity of airway disease has relied on subjectively defined visual evaluation using a variety of different imaging schema. Multi-Slice Computed Tomography (MSCT) offers the potential to quantify the number of peripheral airways subject to mucoid impaction, and therefore allow objective determination of disease severity, progression, and response to treatment. However the sheer number of small airways makes it unrealistic to perform such quantification without automation.

Chronic Obstructive Pulmonary disease (COPD) results in abnormal bronchial wall thickening, lumen dilatation and mucus plugs. Chronic airway inflammation typically results in limitations of airflow, allowing for the accumulation of mucus, especially in the distal airways. Patients with chronic airway disease are clinically followed over time to assess disease progression and response to treatment. In this regard, the ability to obtain an automatic standardized method to rapidly and objectively assess the entire airway tree morphologically, including the extent of mucus plugging, would be of particular clinical value.

Airway analysis and measurements have been a well investigated topic for years. However, no work has been extended to the mucus plugging detection or evaluation although it constitutes an important element to assess disease severity and response to therapy: indeed, airway obstruction with massive mucus plugging accounts for almost 95% of deaths in patients with cystic fibrosis.

SUMMARY OF THE INVENTION

Exemplary embodiments of the invention as described herein generally include methods and systems for automatically detecting the presence and location of mucus plugs within the peripheral airways. A method according to an embodiment of the invention begins with a segmentation of the bronchial tree using previously developed methods. The skeleton-based tree structure is computed and each terminal branch is individually extended using an adaptive threshold algorithm. A local 2-dimensional model is computed based on airway luminal diameter and wall thickness. A few points are selected along the principal axis beyond the terminal branches, to extract 2D cross sections for correlation with a model of mucus plugging. Airway shape is validated with a correlation value, and the lumen distribution is analyzed and compared to the model. A high correlation indicates the presence of a mucus plug. A method according to an embodiment of the invention was tested on 5 datasets containing a total of 40 foci of mucoid impaction. Preliminary results show sensitivity of 77.5% with a specificity of 98.2% and positive predictive value of 66%. A method according to an embodiment of the invention allows radiologists to quickly locate mucus plugs and evaluate their location, number and distribution as well as provide an objective measurement of disease extent.

According to an aspect of the invention, there is provided a method for detecting and localizing mucus plugs in digitized lung images, including providing a digitized lung image volume comprising a plurality of intensities corresponding to a 3-dimensional grid of points, extracting a bronchial tree from said lung image, said bronchial tree comprising a plurality of branching airways terminating at terminal points, providing a model of a 2-dimensional cross section of an airway, selecting an extended point beyond a terminal point of an airway branch in a direction of said airway branch, obtaining a 2-dimensional cross section I of size m×n points from said lung image about said selected point, processing said 2D cross section I by calculating a local neighborhood function for each point in the cross section and forming a union of all local neighborhood functions, and calculating a correlation between processed 2D cross section and said airway model, wherein said correlation is indicative of the presence of a mucus plug within said airway.

According to a further aspect of the invention, extracting a bronchial tree from said lung image comprises segmenting said image volume using an adaptive threshold method and applying an iterative region-growing until terminal points of the airway branches are reached, and skeletonizing to obtain a bronchial tree structure comprising a set of branches, each branch comprising a set of ordered sites.

According to a further aspect of the invention, the method includes computing a distance map along said bronchial tree to obtain a lumen diameter along the bronchial tree.

According to a further aspect of the invention, the airway model is a 2-dimensional p×p image template defined as $$K(x, y) = \begin{pmatrix} k_{0,0} & \cdots & k_{0,p-1} \\ \vdots & \ddots & \vdots \\ k_{p-1,0} & \cdots & k_{p-1,p-1} \end{pmatrix},$$

wherein $x, y \in \mathbb{Z}$, $x \in [0, \ldots, p-1]$, and $y \in [0, \ldots, p-1]$, and wherein $$k_{x,y} = \begin{cases} \Phi_2 & \text{if } h < \|(k_{x,y}, k_{p/2, p/2})\| \le p/2, \\ \Phi_1 & \text{if } h \ge \|(k_{x,y}, k_{p/2, p/2})\|, \\ \Phi_0 & \text{otherwise,} \end{cases}$$

wherein $\Phi_0$, $\Phi_1$, $\Phi_2$ are distinct integers with $\Phi_0<\Phi_1<\Phi_2$, h is an airway lumen diameter, and (p/2)–h is an airway wall thickness.

According to a further aspect of the invention, $\Phi_0=0$, $\Phi_1=1$, and $\Phi_2=2$.

According to a further aspect of the invention, calculating the lumen diameter of said airway model for the airway branch of the extended point comprises selecting a portion of said airway branch, selecting a plurality of cross-sections along said branch portion, obtaining a lumen diameter for each cross section from said distance map, and calculating an average of each cross section lumen diameter.

According to a further aspect of the invention, calculating the wall thickness of said airway model for the airway branch comprises selecting a cross-section at a mid point of said branch portion, projecting a plurality of rays from a skeleton mid point of said cross section, finding a wall thickness from an intensity profile along each ray using a full-width-half-max criteria, and averaging the wall thickness of each ray.

According to a further aspect of the invention, the wall thickness is estimated as 1/(lumen diameter).

According to a further aspect of the invention, the method includes estimating lower and upper intensity thresholds for healthy airways by selecting a cross section at the mid point of said branch, setting said lower intensity threshold $t_1$ the maximum intensity of the lumen in said cross section, estimating the upper intensity threshold $t_2$ by averaging intensity values along said plurality of rays within an estimated wall thickness interval, and estimating a mucus minimum density $d_{muc}$ as a maximum intensity value over said branch portion.

According to a further aspect of the invention, the method includes estimating lower and upper intensity thresholds for healthy airways by setting said thresholds to pre-determined values, and estimating a mucus minimum density as being approximately equal to said lower threshold.

According to a further aspect of the invention, calculating a local neighborhood function for each point in the cross section comprises defining a local p-neighborhood $W^{ij}$ of each point (x, y) of said cross-section as $$W^{ij}(x, y) = \begin{pmatrix} w^{ij}_{0,0} & \cdots & w^{ij}_{0,p-1} \\ \vdots & \ddots & \vdots \\ w^{ij}_{p-1,0} & \cdots & w^{ij}_{p-1,p-1} \end{pmatrix},$$

$$\forall i \in [0, \ldots, m-1], \forall j \in [0, \ldots, n-1],$$

wherein said union of all local neighborhood functions is $$\bigcup_{i,j} W^{ij}$$

for $i \in [0, \ldots, m-1]$ and $j \in [0, \ldots, n-1]$, wherein, $\forall x \in [0, \ldots, p-1]$, $\forall y \in [0, \ldots, p-1]$, for a clean airway, $$w^{ij}_{x,y} \begin{cases} \Phi_2 & \text{if } t_2 \leq I\left(i - \left(\frac{p-1}{2}\right) + x, j - \left(\frac{p-1}{2}\right) + y\right) \text{ and } k_{i,j} \geq \Phi_2, \\ \Phi_1 & \text{if } t_1 \geq I\left(i - \left(\frac{p-1}{2}\right) + x, j - \left(\frac{p-1}{2}\right) + y\right) \text{ and } k_{i,j} \geq \Phi_1, \\ \Phi_0 & \text{otherwise,} \end{cases}$$

wherein $t_1$ and $t_2$ are respectively lower and upper intensity bounds for a healthy lumen, and for a mucus-filled airway, $$w^{ij}_{x,y} \begin{cases} \Phi_2 & \text{if } t_2 \leq I\left(i - \left(\frac{p-1}{2}\right) + x, j - \left(\frac{p-1}{2}\right) + y\right) \text{ and } k_{i,j} \geq \Phi_2, \\ \Phi_1 & \text{if } d_{muc} \geq I\left(i - \left(\frac{p-1}{2}\right) + x, j - \left(\frac{p-1}{2}\right) + y\right) \text{ and } k_{i,j} \geq \Phi_1, \\ \Phi_0 & \text{otherwise,} \end{cases}$$

wherein $d_{muc}$ is a mucus minimum density.

According to a further aspect of the invention, the correlation C between processed 2D cross section and said airway model is calculated as $$C^{ij} = \frac{\sum_{x=0}^{p-1} \sum_{y=0}^{p-1} w^{ij}_{x,y}}{\sum_{x=0}^{p-1} \sum_{y=0}^{p-1} k_{x,y}}$$

wherein $0 \leq C^{ij} \leq 1$, and wherein a correlation greater a predefined first tolerance value is indicative of a mucus plug and a correlation greater a predefined second tolerance value less than said first tolerance value is indicative of a clean airway.

According to another aspect of the invention, there is provided a method for detecting and localizing mucus plugs in digitized lung images, including providing a digitized lung image volume comprising a plurality of intensities corresponding to a 3-dimensional grid of points, correlating a p×p airway model to an m×n 2D airway cross section I extracted from said lung image from $$C^{ij} = \frac{\sum_{x=0}^{p-1} \sum_{y=0}^{p-1} w^{ij}_{x,y}}{\sum_{x=0}^{p-1} \sum_{y=0}^{p-1} k_{x,y}},$$

wherein $0 \leq C^{ij} \leq 1$, $x, y \in Z, x \in [0, \ldots, p-1]$, and $y \in [0, \ldots, p-1]$, $$k_{x,y} = \begin{cases} 2 & \text{if } h < \|(k_{x,y}, k_{p/2,p/2})\| \leq p/2, \\ 1 & \text{if } h \geq \|(k_{x,y}, k_{p/2,p/2})\|, \\ 0 & \text{otherwise,} \end{cases}$$

wherein h is a lumen diameter of said airway, and (p/2)–h is a wall thickness of said airway, wherein for a clean airway, $$w^{ij}_{x,y} \begin{cases} 2 & \text{if } t_2 \leq I\left(i - \left(\frac{p-1}{2}\right) + x, j - \left(\frac{p-1}{2}\right) + y\right) \text{ and } k_{i,j} \geq 2, \\ 1 & \text{if } t_1 \geq I\left(i - \left(\frac{p-1}{2}\right) + x, j - \left(\frac{p-1}{2}\right) + y\right) \text{ and } k_{i,j} \geq 1, \\ 0 & \text{otherwise,} \end{cases}$$

wherein $t_1$ and $t_2$ are respectively lower and upper intensity bounds for a healthy lumen, wherein for a mucus-filled airway, $$w_{x,y}^{ij} = \begin{cases} 2 & \text{if } t_2 \le I\left(i-\left(\frac{p-1}{2}\right)+x,\ j-\left(\frac{p-1}{2}\right)+y\right) \text{ and } k_{i,j} \ge 2, \\ 1 & \text{if } d_{muc} \ge I\left(i-\left(\frac{p-1}{2}\right)+x,\ j-\left(\frac{p-1}{2}\right)+y\right) \text{ and } k_{i,j} \ge 1, \\ 0 & \text{otherwise,} \end{cases}$$

wherein $d_{muc}$ is a mucus minimum density, and wherein a correlation greater a predefined high tolerance value is indicative of a mucus plug and a correlation greater a predefined low tolerance value less than said first tolerance value is indicative of a clean airway.

According to a further aspect of the invention, the method includes extracting a bronchial tree from said lung image, said bronchial tree comprising a plurality of branching airways terminating at terminal points; and computing a distance map along said bronchial tree to obtain a lumen diameter along the bronchial tree.

According to a further aspect of the invention, extracting said m×n 2D airway cross section I comprises selecting an extended point beyond a terminal point of an airway branch in a direction of said airway branch; extracting said 2-dimensional cross section I of size m×n points from said lung image about said extended point;

According to a further aspect of the invention, the method includes forming a union of all local neighborhood functions $$\bigcup_{i,j} W^{ij}$$

for $i \in [0, \ldots, m-1]$ and $j \in [0, \ldots, n-1]$ wherein $$W^{ij}(x,y) = \begin{pmatrix} w_{0,0}^{ij} & \cdots & w_{0,p-1}^{ij} \\ \vdots & \ddots & \vdots \\ w_{p-1,0}^{ij} & \cdots & w_{p-1,p-1}^{ij} \end{pmatrix},$$

$\forall\, i \in [0,\ldots,m-1],\ \forall\, i \in [0,\ldots,n-1].$

According to another aspect of the invention, there is provided a program storage device readable by a computer, tangibly embodying a program of instructions executable by the computer to perform the method steps for detecting and localizing mucus plugs in digitized lung images.

DETAILED DESCRIPTION OF EXEMPLARY EMBODIMENTS

Figure 1:
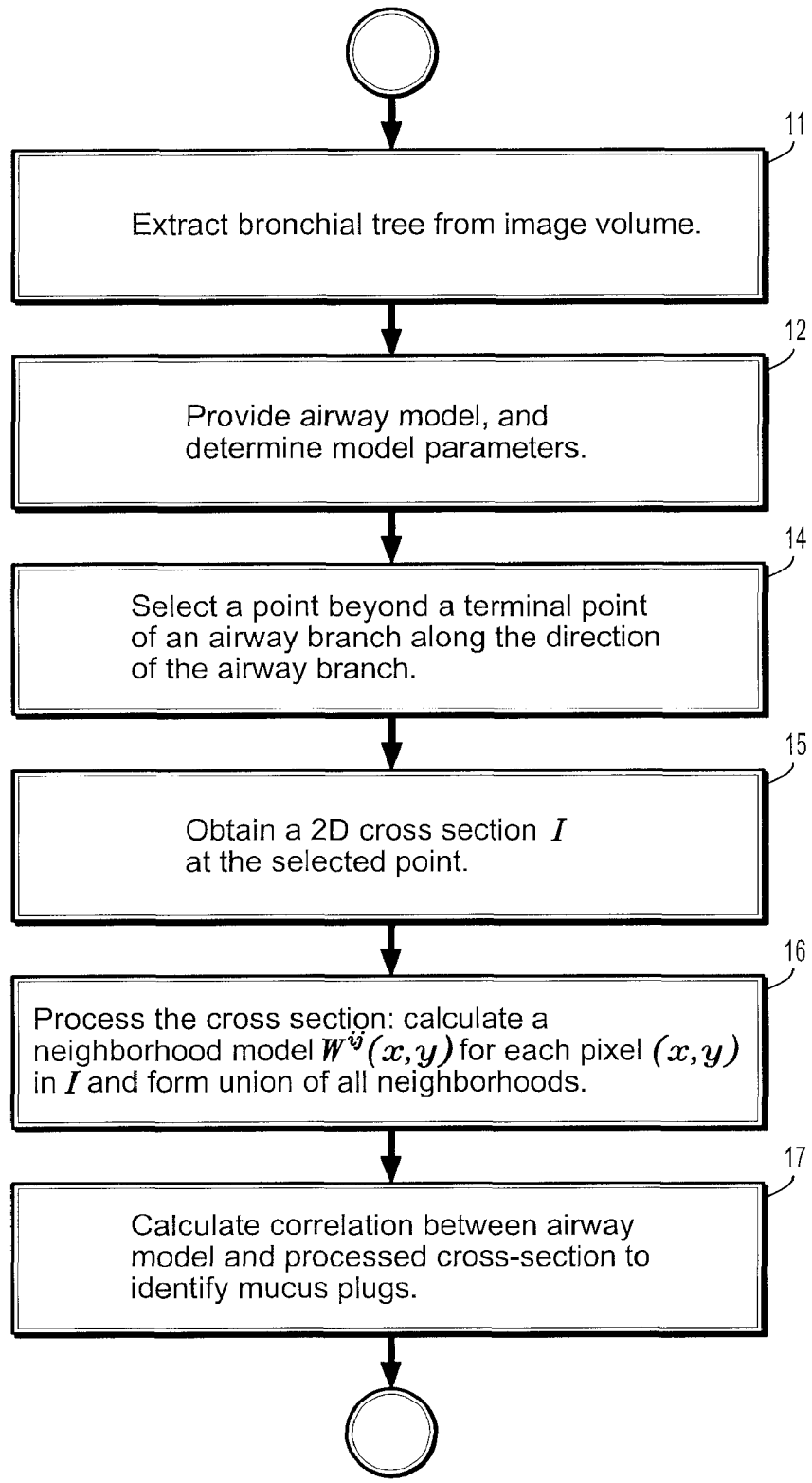
FIG. 1 is a flow chart of a method for detection and location of mucus plugs that obstruct the airway tree, according to an embodiment of the invention.

Exemplary embodiments of the invention as described herein generally include systems and methods for detection and location of mucus plugs that obstruct the airway tree. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A flow chart of a method according to an embodiment of the invention for detection and location of mucus plugs that obstruct the airway tree is presented in FIG. 1. Referring to the figure, a method begins at step 11 by extracting a bronchial tree from a Multi-Slice Computed Tomography (MSCT) dataset. Bronchial tree extraction is accomplished by segmenting the bronchial tree and computing a tree model using adaptive threshold and region growing algorithms. The tree model serves as a work-base for acquiring the local direction of airway branches. At each terminal branch, an interactive adaptive threshold region-growing algorithm is applied to assure that the termination of the branch is reached. An airway model of an airway branch is provided at step 12. An exemplary airway model according to an embodiment of the invention is characterized by a lumen diameter and a wall thickness, and these parameters are determined from the bronchial tree data. At step 14, a bronchial tree terminal point is selected, and an extended point is selected beyond the terminal branch along a direction vector calculated from the direction of the branch. A 2D cross-section is extracted about the extended point at step 15. Each cross section is processed at step 16 to calculate a neighborhood model about each pixel in the cross section, and a processed cross section is formed from the union of these neighborhood models. At step 17 the neighborhood models are matched to the airway model of mucus plugging computed from the termination of the branch, and a correlation is calculated. The highest correlation value indicates the best match shape-wise and the resemblance in lumen analysis between the model at the terminal branch and at the selected location suggests the presence of mucus plug. Steps 14, 15, 16, and 17 are repeated for all terminal points. These steps will be described in detail herein below.

Bronchial Tree Extraction

Figure 2:
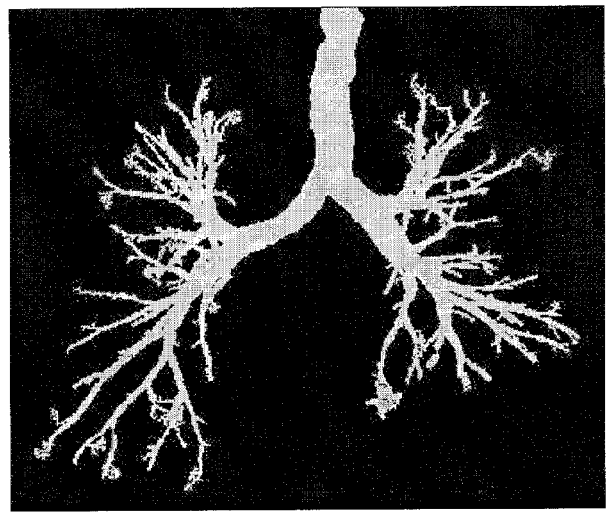
FIG. 2 depicts an exemplary extended bronchial tree segmentation result, according to an embodiment of the invention.

The bronchial tree is obtained by a two step process of segmentation and skeletonization. The bronchial tree segmentation according to an embodiment of the invention applies an adaptive threshold to an image volume and then extends the obtained result further by applying region-growing to the tips of the terminal branches. An exemplary extended bronchial tree segmentation result is shown in FIG. 2. Further adjustments provide automatic filtering and speed improvements.

In additional, a skeleton is computed on the segmented image volume and refined to obtain a description of the tree's branch structure suitable for navigation and quantitative analysis. Methods of segmentation and skeletonization are known in the art. The tree structure that results from the skeletonization describes the airways as a series of paths and orientations. The tree structure T is composed of branches $b_i \in B$ and sites $s^i_k \in b_i$ and can be expressed as follows:

$$T = \bigcup_i b_i,$$

with $i \in [0, \ldots, N]$ and N, the number of branches in the computed tree, and $$b_i = \bigcup_i s^i_k,$$

with $k \in [0, \ldots, K]$ and K, the number of sites in the $i^{th}$ branch, the distance between $s^i_k$ and $s^i_{k-1}$ being the minimum delta of the image. A path is a series of branches $b_i$ starting from a pre-defined root branch, in this case the trachea, and terminating with a terminal branch. A terminal branch is a branch that does not branch further.

During segmentation, if a proximal airway is obstructed, missing airway branches can be detected using a Selective Marking and Depth Constrained (SMDC) cost-connection method. A cost connection operator fills the valleys in the lungs represented by the air zones (parenchyma and airways). The bronchial tree is then specifically marked using a new relief function derived from the volume, a processed function $Of(x)$, with O being an extensive operator such that $O:R \to R$, $Of(x) \geq f(x)$, $\forall x \in \mathrm{supp}(f)$, and a restricted set of regional minima of $Of$. For efficiency purposes, the same SMDC algorithm is applied on a volume of interest defined around proximal branches of the tree if they correspond to terminal branches. This allows selecting candidates for airways that were not previously detected during initial segmentation. The rest of airway tree is then grown out from these candidates.

Mucus Pattern Definition

A method according to an embodiment of the invention applies the mucus detection process along the segmented bronchial tree. Although this approach is limited to detecting mucus within the automatic segmentation result, and therefore offers a non-exhaustive set of mucus plug locations throughout the lungs, it can still assess partial and total airway obstructions in the first several generations of airways. Along the branch direction, a 2D mucus model is correlated 2D transverse slices and the response is monitored to detect plugs.

Local 2D Airway Model

Figure 3:
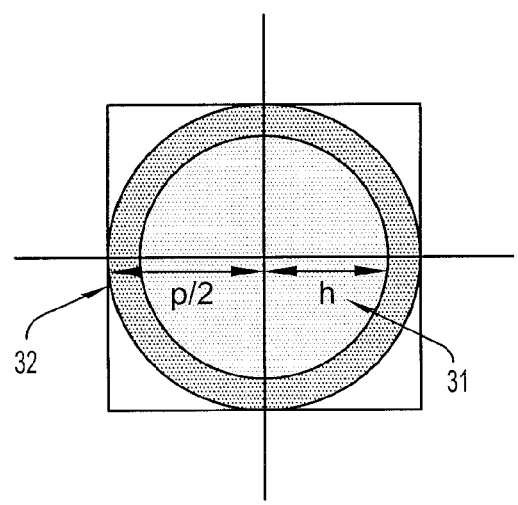
FIG. 3 depicts an exemplary airway model, according to an embodiment of the invention.

An airway model according to an embodiment of the invention is 2-dimensional and represents an ideal shape of the lumen or mucus impaction in a binary form. FIG. 3 depicts an exemplary airway model. The lumen 31 is shown as light gray, and the airway wall 32 is dark gray. The airway lumen and wall areas are respectively associated with a mean intensity, a standard deviation and a threshold. As shown in the figure, an airway model K(x, y) is a discrete 2D image containing a circular shape, with lumen diameter 2h and wall thickness p/2–h. The airway cross-section is modeled as a hollow circle with a thick perimeter. The inside area represents the lumen while the perimeter represents the airway wall. These two features are the model's parameters, and are adjusted to the airway branch that is reviewed when the model is applied. The size of the lumen as well as an estimate of the wall thickness of the branch cross section are used to determine these parameters. Using the bronchial tree segmentation, a distance map is computed to obtain the lumen diameter along the whole segmentation. The distance map computes the minimum distance from every bronchial tree voxel to the background. For the case of tubular regions such as airways, the maximum distance can be assumed to the radius of the airways.

Specifically, a local 2D airway model according to an embodiment of the invention is a 2-dimensional p×p image template expressed as follow:

$$K(x, y) = \begin{pmatrix} k_{0,0} & \cdots & k_{0,p-1} \\ \vdots & \ddots & \vdots \\ k_{p-1,0} & \cdots & k_{p-1,p-1} \end{pmatrix} \quad (1)$$

with x, y∈Z, x∈[0, . . . , p−1], and y∈[0, . . . , p−1], and with $$k_{x,y} = \begin{cases} 2 & \text{if } h < \|(k_{x,y}, k_{p/2,p/2})\| \leq p/2, \\ 1 & \text{if } h \geq \|(k_{x,y}, k_{p/2,p/2})\|, \\ 0 & \text{otherwise.} \end{cases} \quad (2)$$

Note that the values of 0, 1, and 2 used in the airway model are arbitrary, and those skilled in the art will recognize that other values having the same ordering can be used according to other embodiments of the invention. It is further to be understood, however, that the circular model depicted in FIG. 3 and defined above is exemplary and non-limiting, and is used for illustrative purposes only. According to other embodiments of the invention, other shapes, such as ellipses or higher order curves, can be used for the airway model.

Figure 4:
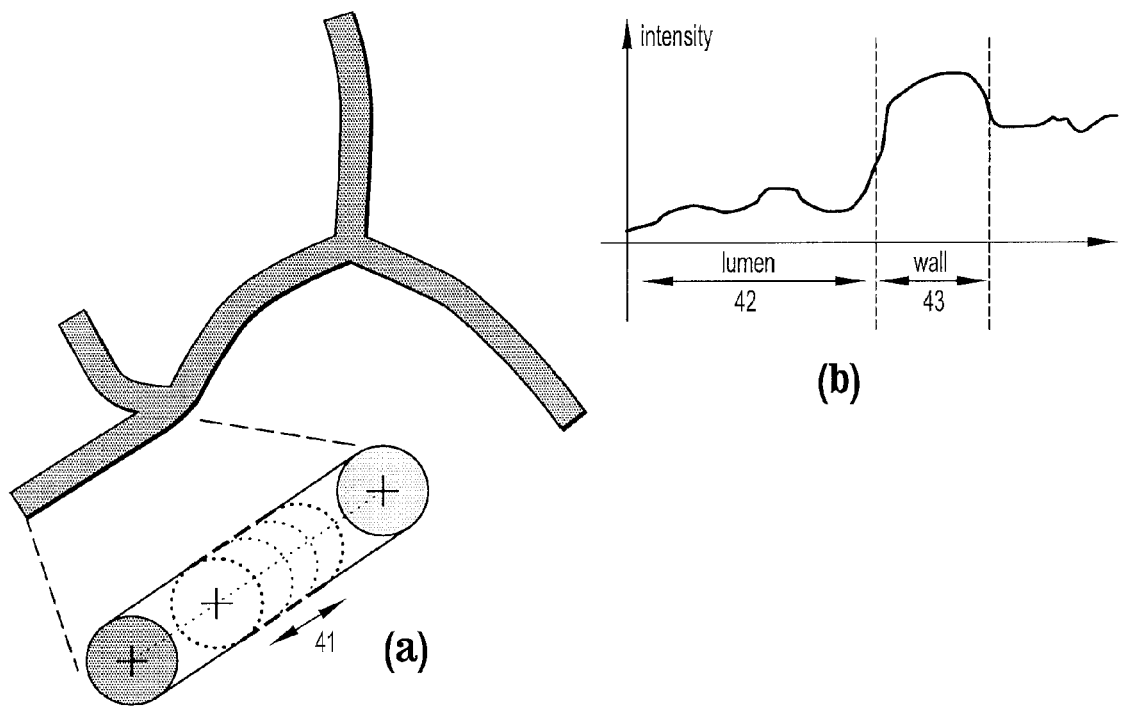
FIGS. 4(a)-(b) depict a section of an airway branch and a cross sectional intensity profile, according to an embodiment of the invention.

A first step in using the model according to an embodiment of the invention is to calculate the lumen diameter and wall thickness. FIG. 4(*a*) depicts a section of an airway branch, where a portion $S_i$ 41 of length $l_i$ in dotted lines represents the center half of the branch, while FIG. 4(*b*) illustrates an exemplary intensity profile used to estimate the lumen diameter 42 as well as airway wall 43. Let $CS^i_k$ be the trilinear interpolated cross-section at the site $s^i_k$ of the branch $b_i$ of length K. The $S_i$ are defined as the series of airway cross sections $CS^i_k$ comprised of the middle 3D portion of the branch $b_i$. An exemplary, non-limiting middle portion can be defined with $$k \in \left[\frac{K}{4}, \frac{3K}{4}\right],$$

with a length $l_i$ of $S_i$ is defined as:

$$l_i = \frac{L_{branch}(b_i)}{2}, \quad (3)$$

where $L_{branch}(b_i)$ is the total length of the branch $b_i$, as shown in FIG. 4(a). Using the sites $s^i_k$ within the 3D portion $S_i$ as well as the previously computed distance map, the cross section diameter value are calculated and averaged to obtain the lumen diameter. The wall thickness is estimated using the middle cross section of the branch. A plurality of rays are projected starting from the skeleton middle site $s_{mid}$ of the branch and a profile analysis as is performed using a Full-Width-Half-Max (FWHM) method. The wall thickness is estimated as an average of the thickness found by the rays. An exemplary, non-limiting number of rays is four.

In case the FWHM method does not give satisfactory results for the wall thickness, due to partial volume effect for instance, it is assumed that the airway is normal and the wall thickness is set accordingly, with a ratio of one over the lumen diameter. Such estimation has less importance in this mucus detection application since the wall is primarily need to check whether the lumen is filled and consequently if high density tissues surround the luminal area.

According to an embodiment of the invention, a next step is to determine the grayscale densities that characterize healthy and mucus impacted lumens. The low and a high thresholds are defined using the cross section of the branch under review located at site $s^i_{K/2}$ in the middle of the branch i. The low threshold $t_1$ is set to the maximum value of the lumen within the 3D portion $S_i$. The high threshold $t_2$ is computed using the ray profiles by averaging the values of the determined wall thickness interval. If the values or profiles are unstable, for example due to partial volume effects, the low threshold $t_1$ can be set to 125 grayscale units and the high threshold $t_2$ can be set to 300 grayscale units.

To search for mucus plugs, observe that mucus in the airway appears as a bright region as compared to a dark region for air in the airway. Thus the mucus can be located by regions of intensity than air. A mucus minimum density $d_{muc}$ is defined as the maximum value of interior of the airway portion $S_i$. Again, in case of instability in the computation of the profiles, this minimum density $d_{muc}$ can be set to $t_1$.

Detection of Mucus Plugs

From the previous segmentation, the terminal points will be collected and associated with a direction vector based on the orientation of the branch to which they belong. The search for mucus is performed along the direction of branch i in conjunction with the airway model, described above. Initially, all terminal sites can be considered healthy. At the tip of the terminal branch or terminal site $s^i_{K-1}$, the branch is extended along its direction by one isotropic voxel unit, the minimum delta length of the image, to obtain a candidate point $s_{cand}$. At $s_{cand}$, a trilinear interpolated 2D cross-section I of size (m,n) is computed and processed to form $I_{proc}$. The airway model is placed onto and correlated with the processed cross section image $I_{proc}$. The correlation is used to match the shape of the airway model as well as the intensity distribution in the cross section image $I_{proc}$. A tolerance is set both locally and globally for a clean airway and for a mucus-impacted airway respectively. Here, clean means not filled with secretions. Other aspects of airway health, such as dilatation and inflamed walls, were not considered in this embodiment, although these aspects can be accounted for according to other embodiments of the invention.

Matching the model with the mucus can be performed in two phases. In a first phase, the processed image $I_{proc}$ is computed from the 2D cross section I. Each local neighborhood through the whole cross section image I is compared to the airway model, placed at the center of the image, to match both its shape and its grey scale distribution. The image pixels are compared with the corresponding model pixels that belong to the lumen or wall. The intensity of lumen pixels of image I should fall within one standard deviation of the lumen model, and the intensity of the wall pixels should do the same. The thresholds $t_1$ and $t_2$ previously computed are used to handle the small airways and the intensity variations between a small number of pixels. The number of pixels that are within the standard deviation is verified against the predefined mucus tolerance to validate the presence of secretion that obstructing the airway. Basically, for every point of the image I that also matches an airway model point, whether its local neighborhood belongs to a portion of the airway is determined by verifying the density value of the neighboring points.

More specifically, according to an embodiment of the invention, a local p-neighborhood $W^{ij}$ of each pixel of image I(i,j) can be defined as $$W^{ij}(x, y) = \begin{pmatrix} w^{ij}_{0,0} & \cdots & w^{ij}_{0,p-1} \\ \vdots & \ddots & \vdots \\ w^{ij}_{p-1,0} & \cdots & w^{ij}_{p-1,p-1} \end{pmatrix}, \quad (4)$$

$\forall i \in [0, \ldots, m-1], \forall j \in [0, \ldots, n-1]$, where $W^{ij}$ varies depending on the target (healthy or mucus-filled airway). For the case of clean airways, there is $$w^{ij}_{x,y} = \begin{cases} 2 & \text{if } t_2 \leq I\left(i - \left(\frac{p-1}{2}\right) + x, j - \left(\frac{p-1}{2}\right) + y\right) \text{ and } k_{i,j} \geq 2, \\ 1 & \text{if } t_1 \geq I\left(i - \left(\frac{p-1}{2}\right) + x, j - \left(\frac{p-1}{2}\right) + y\right) \text{ and } k_{i,j} \geq 1, \\ 0 & \text{otherwise,} \end{cases} \quad (5)$$

$\forall x \in [0, \ldots, p-1], \forall y \in [0, \ldots, p-1]$. In (5), the threshold values respectively substitute for the mean and standard deviation of the lumen and wall because small airways are targeted with small variations in the intensity within the airway lumen and wall.

For the case of mucus-filled airway, there is:

$$w^{ij}_{x,y} = \begin{cases} 2 & \text{if } t_2 \leq I\left(i - \left(\frac{p-1}{2}\right) + x, j - \left(\frac{p-1}{2}\right) + y\right) \text{ and } k_{i,j} \geq 2, \\ 1 & \text{if } d_{muc} \geq I\left(i - \left(\frac{p-1}{2}\right) + x, j - \left(\frac{p-1}{2}\right) + y\right) \text{ and } k_{i,j} \geq 1, \\ 0 & \text{otherwise,} \end{cases} \quad (6)$$

$\forall x \in [0, \ldots, p-1], \forall y \in [0, \ldots, p-1]$, with $d_{muc}$ defined as above.

Note that, as with the airway model, the values of 0, 1, and 2 used to define the p-neighborhood are arbitrary, and those skilled in the art will recognize that other values can be used according to other embodiments of the invention, as long as they are consistent with the values used or the airway model.

According to an embodiment of the invention, a tolerance is statistically defined to distinguish a healthy airway from a pathological airway filled with mucus. The tolerance is lower for a healthy airway because one is not looking at a filled lumen. The model should match mucus with high intensity for the lumen. Thus, according to an embodiment of the invention, for mucus detection, tolerance is set to about 0.9, meaning that 90% of the pixels in the neighborhood $W^{ij}$ should correspond to the intensity distribution expressed in this model distribution to validate the neighborhood $W^{ij}$. If the model does not fit completely, the airway is said to be clean. Specifically, a tolerance of at least about 66% is considered to indicate a clean airway. If a cross section is recognized as a clean airway, the location can be used to extend the airway branch and keep looking for mucus. If the minimum tolerance is not reached, $W^{ij}$ is set to zero everywhere.

The processed cross section $I_{proc}$ is the union of all neighborhoods $W^{ij}$, $$I_{proc}(i, j) = \bigcup_{i,j} W^{ij}, \text{ with } i \in [0, \ldots, m-1] \text{ and } j \in [0, \ldots, n-1]. \quad (7)$$

The segmentation of the bronchial tree rarely reaches the actual end of the peripheral airways. The use of the airway model can contribute to further extension of the branch. In case the image I matches an airway cross section, the process is repeated by looking for another set of candidates starting from the cross-section image I.

In a second phase of a mucus detection according to an embodiment of the invention, a correlation between the airway model and the processed cross section is computed. The correlation C between $I_{proc}$ and the airway model can be defined as $$C^{ij} = \frac{s}{S} = \frac{\sum_{x=0}^{p-1}\sum_{y=0}^{p-1} w^{ij}_{x,y}}{\sum_{x=0}^{p-1}\sum_{y=0}^{p-1} k_{x,y}} \quad (8)$$

where $0 \leq C^{ij} \leq 1$, s is the sum of the elements of $W^{ij}$ and S is the sum of the elements of K. A correlation greater than the tolerance of about 0.9 is indicative of the presence of mucus, while a correlation greater than about 0.66 is indicative of a clean airway.

Figure 5:
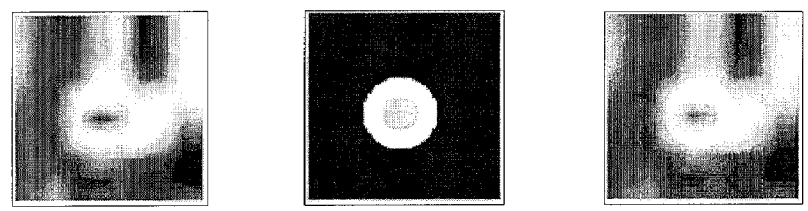
FIGS. 5(a)-(e) illustrate a mucus detection process according to an embodiment of the invention.

FIGS. 5(a)-(e) illustrate a mucus detection process according to an embodiment of the invention. FIG. 5(a) shows a middle cross section to determine wall and luminal diameters. FIG. 5(b) depicts an airway model. FIG. 5(c) shows the superposition of the airway and airway model. FIG. 5(d) depicts the cross section at the candidate point, and FIG. 5(e) shows the processed image $I_{proc}$ focused on a mucus-plugged like airway.

Tests and Results

A method according to an embodiment of the invention was tested using 5 high resolution volumetric CT data sets with images obtained from the thoracic inlet to the hemidiaphragms in a single breathhold period using a 16-slice detector scanner. Contiguous 1 mm sections were prospectively reconstructed with near isotropic resolution, using a sharp image kernel acquired with standard radiation dosage. Anonymized data were then transferred to a Dell Workstation Pentium 4 Xeon III, 1.7 GHz CPU, with 2 GB of RAM for evaluation. All studies were acquired as part of routine clinical assessment of patients with known or suspected chronic airway disease.

In order to assess efficacy, the status of each terminal branch in the extracted airway segmentations was assessed. This gave rise to 929 foci of potential mucoid impaction, an average of 185 per patient. In all, there were 40 terminal branch locations in the 5 datasets that actually contained mucus plugs. The presence of mucoid impacted airways was subsequently validated by review of these images by an experienced thoracic radiologist.

Figure 6:
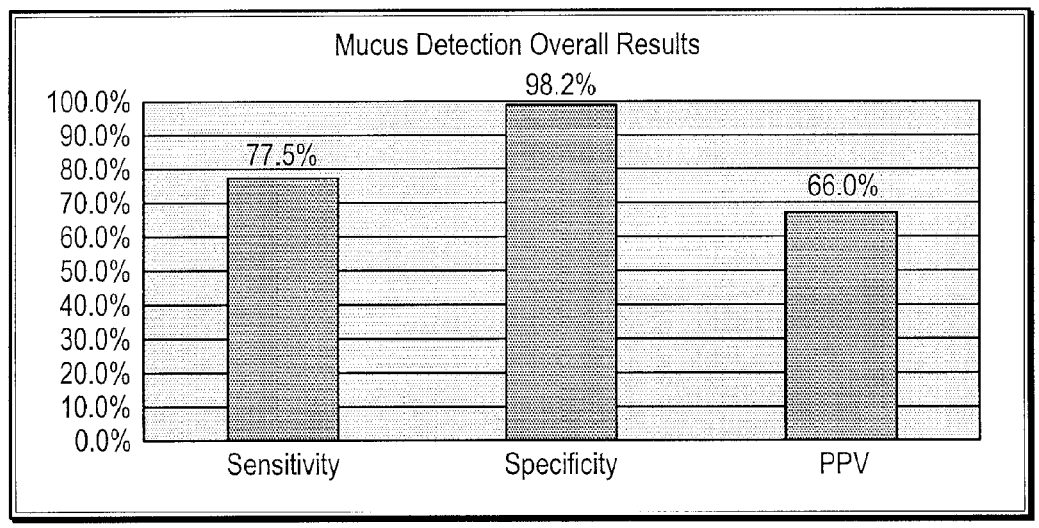
FIGS. 6(a)-(b) are a table and bar graph depicting results of a mucus detection process according to an embodiment of the invention.

Results are reported in the table of FIG. 6(a) and bar graph of FIG. 6(b). A method according to an embodiment of the invention detected 31 out of 40 of the locations identified as obstructed by mucus plugs for a sensitivity of 77.5%. Of the 889 branches without airway obstruction, 873 were correctly classified as negative, resulting in a specificity of 98.2%. There were 16 false positive detections yielding a positive predictive value (PPV) of 66%.

Figure 7:
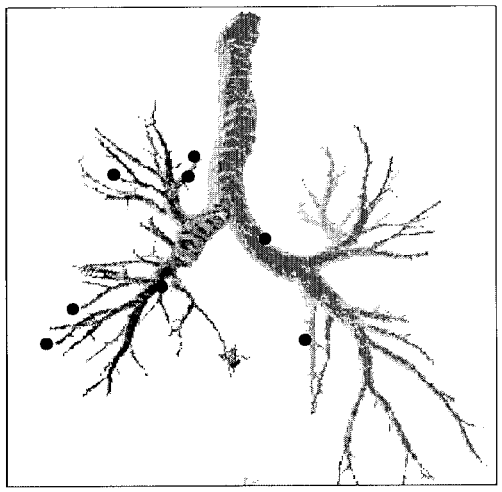
FIG. 7 shows 3D renderings of bronchial tree with mucus locations, according to an embodiment of the invention.
Figure 7:
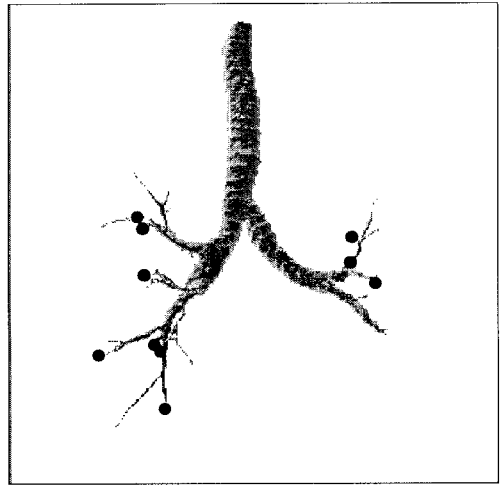
Figure 7:
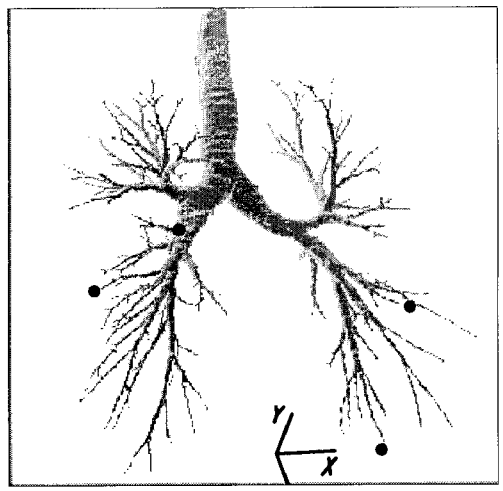
Figure 7:
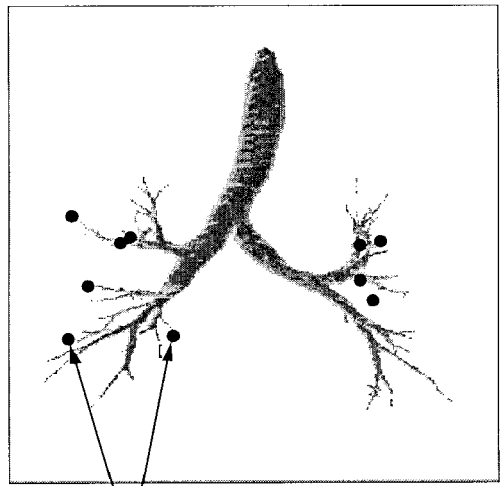
Figure 8:
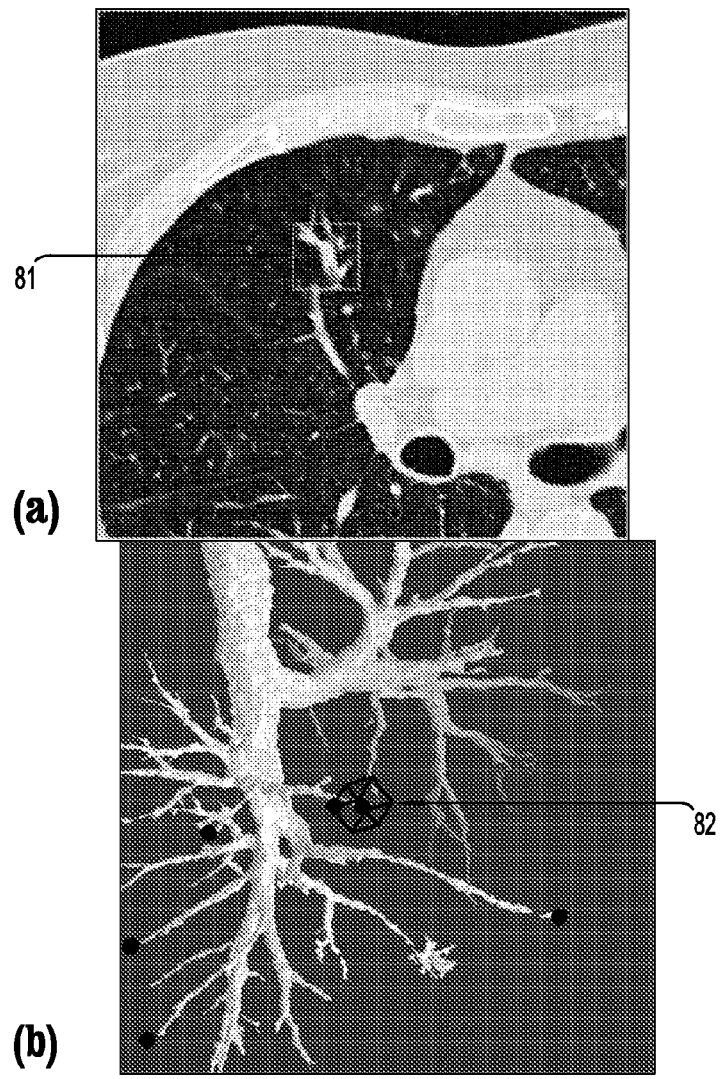
FIGS. 8(a)-(b) is a visualization of bronchial tree with mucus plugs location, according to an embodiment of the invention.

3D visualization allows the radiologists to quickly locate the mucoid foci and determine their extent. FIG. 7 shows four 3D renderings of bronchial tree with mucus locations, with spheres indicated to represent the detected mucus plugs. To avoid obscuring the drawing, only 2 such spheres 71 are indicated by arrows in the figure. Corresponding locations on axial slices are reached by selecting one of the mucus-locating spheres FIGS. 8(a)-(b) is a 3D visualization of bronchial tree with mucus plugs location. FIG. 8(a) shows a severe mucus plug on corresponding axial slice shown by square (81), while FIG. 8(b) shows a selected mucoid impaction marked by surrounding white cube (82).

System Implementation

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 9:
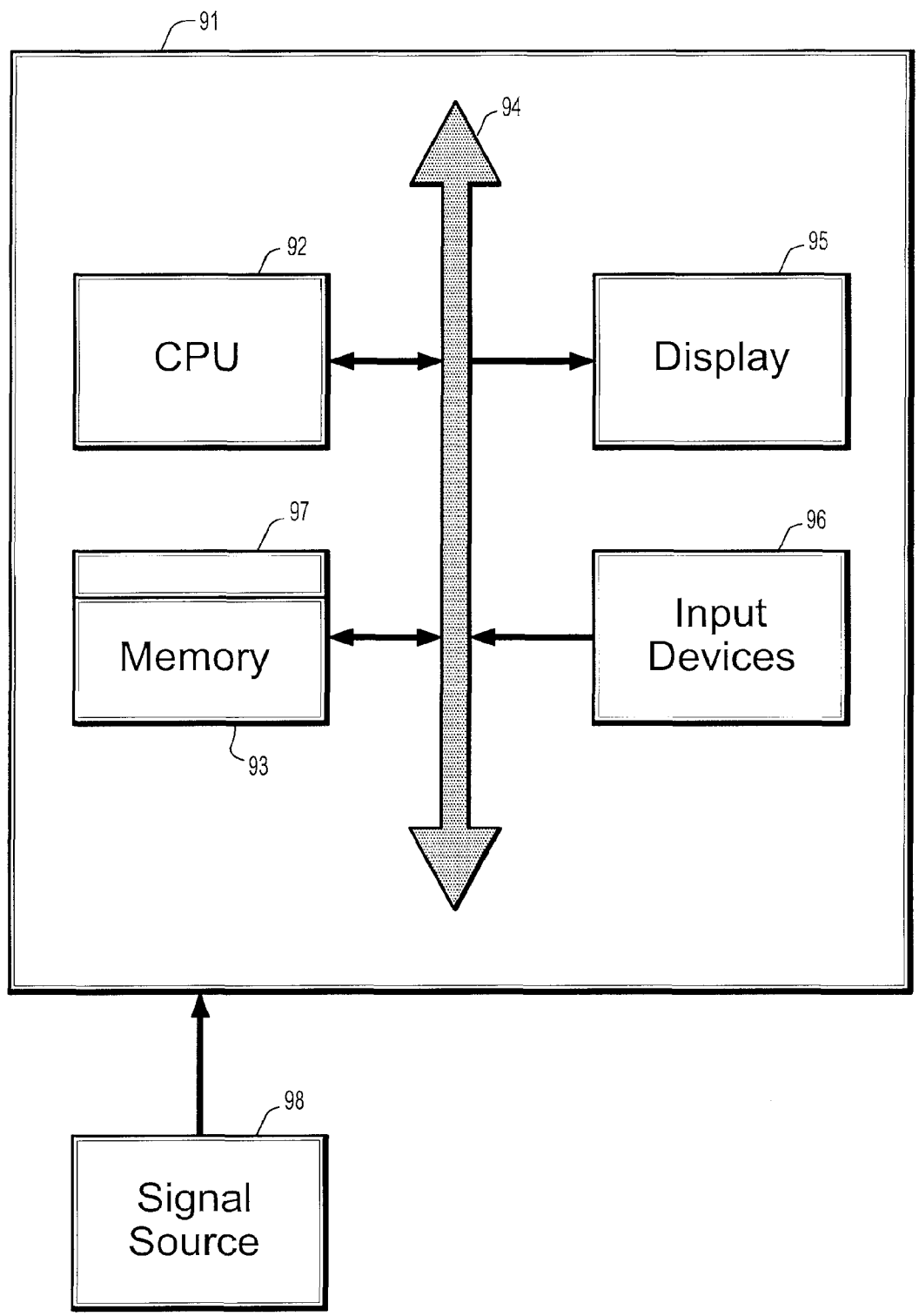
FIG. 9 is a block diagram of an exemplary computer system for implementing a method for detection and location of mucus plugs that obstruct the airway tree, according to an embodiment of the invention.

FIG. 9 is a block diagram of an exemplary computer system for implementing a method for detecting and locating mucus plugs that obstruct the airway tree according to an embodiment of the invention. Referring now to FIG. 9, a computer system 91 for implementing the present invention can comprise, inter alia, a central processing unit (CPU) 92, a memory 93 and an input/output (I/O) interface 94. The computer system 91 is generally coupled through the I/O interface 94 to a display 95 and various input devices 96 such as a mouse and a keyboard. The support circuits can include circuits such as cache, power supplies, clock circuits, and a communication bus. The memory 93 can include random access memory (RAM), read only memory (ROM), disk drive, tape drive, etc., or a combinations thereof. The present invention can be implemented as a routine 97 that is stored in memory 93 and executed by the CPU 92 to process the signal from the signal source 98. As such, the computer system 91 is a general purpose computer system that becomes a specific purpose computer system when executing the routine 97 of the present invention.

The computer system 91 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for detecting and localizing mucus plugs in digitized lung images comprising the steps of:
   providing a digitized lung image volume comprising a plurality of intensities corresponding to a 3-dimensional grid of points;
   extracting a bronchial tree from said lung image, said bronchial tree comprising a plurality of branching airways terminating at terminal points;
   providing a model of a 2-dimensional cross section of an airway;
   selecting an extended point beyond a terminal point of an airway branch in a direction of said airway branch;
   obtaining a 2-dimensional cross section I of size m×n points from said lung image about said selected point;
   processing said 2D cross section I by calculating a local neighborhood function for each point in the cross section and forming a union of all local neighborhood functions; and
   calculating a correlation between processed 2D cross section and said airway model, wherein said correlation is indicative of the presence of a mucus plug within said airway.

2. The method of claim 1, wherein extracting a bronchial tree from said lung image comprises segmenting said image volume using an adaptive threshold method and applying an iterative region-growing until terminal points of the airway branches are reached, and skeletonizing to obtain a bronchial tree structure comprising a set of branches, each branch comprising a set of ordered sites.

3. The method of claim 1, further comprising computing a distance map along said bronchial tree to obtain a lumen diameter along the bronchial tree.

4. The method of claim 3, wherein said airway model is a 2-dimensional p×p image template defined as $$K(x, y) = \begin{pmatrix} k_{0,0} & \cdots & k_{0,p-1} \\ \vdots & \ddots & \vdots \\ k_{p-1,0} & \cdots & k_{p-1,p-1} \end{pmatrix},$$

wherein x, y∈Z, x∈[0, ..., p−1], and y∈[0, ... p−1], and wherein $$k_{x,y} = \begin{cases} \Phi_2 & \text{if } h < \|(k_{x,y}, k_{p/2,p/2})\| \le p/2, \\ \Phi_1 & \text{if } h \ge \|(k_{x,y}, k_{p/2,p/2})\|, \\ \Phi_0 & \text{otherwise,} \end{cases}$$

wherein $\Phi_0$, $\Phi_1$, $\Phi_2$ are distinct integers with $\Phi_0 < \Phi_1 < \Phi_2$, h is an airway lumen diameter, and (p/2)−h is an airway wall thickness.

5. The method of claim 4, wherein $\Phi_0 = 0$, $\Phi_1 = 1$, and $\Phi_2 = 2$.

6. The method of claim 4, wherein calculating the lumen diameter of said airway model for the airway branch of the extended point comprises selecting a portion of said airway branch, selecting a plurality of cross-sections along said branch portion, obtaining a lumen diameter for each cross section from said distance map, and calculating an average of each cross section lumen diameter.

7. The method of claim 6, wherein calculating the wall thickness of said airway model for the airway branch comprises selecting a cross-section at a mid point of said branch portion, projecting a plurality of rays from a skeleton mid point of said cross section, finding a wall thickness from an intensity profile along each ray using a full-width-half-max criteria, and averaging the wall thickness of each ray.

8. The method of claim 6, wherein the wall thickness is estimated as 1/(lumen diameter).

9. The method of claim 7, further comprising estimating lower and upper intensity thresholds for healthy airways by selecting a cross section at the mid point of said branch, setting said lower intensity threshold $t_1$ to the maximum intensity of the lumen in said cross section, estimating the upper intensity threshold $t_2$ by averaging intensity values along said plurality of rays within an estimated wall thickness interval, and estimating a mucus minimum density $d_{muc}$ as a maximum intensity value over said branch portion.

10. The method of claim 7, further comprising estimating lower and upper intensity thresholds for healthy airways by setting said thresholds to pre-determined values, and estimating a mucus minimum density as being approximately equal to said lower threshold.

11. The method of claim 4, wherein calculating a local neighborhood function for each point in the cross section comprises defining a local p-neighborhood $W^{ij}$ of each point (x, y) of said cross-section as $$W^{ij}(x, y) = \begin{pmatrix} w^{ij}_{0,0} & \cdots & w^{ij}_{0,p-1} \\ \vdots & \ddots & \vdots \\ w^{ij}_{p-1,0} & \cdots & w^{ij}_{p-1,p-1} \end{pmatrix},$$

$$\forall i \in [0, \ldots, m-1], \forall j \in [0, \ldots, n-1],$$

wherein said union of all local neighborhood functions is $$\bigcup_{i,j} W^{ij}$$

for i∈[0, ..., m−1] and j∈[0, ..., n−1], wherein, ∀x∈[0, ..., p−1], ∀y∈[0, ..., p−1], for a clean airway, $$w_{x,y}^{ij} = \begin{cases} \Phi_2 & \text{if } t_2 \leq I\left(i-\left(\frac{p-1}{2}\right)+x, j-\left(\frac{p-1}{2}\right)+y\right) \text{ and } k_{i,j} \geq \Phi_2, \\ \Phi_1 & \text{if } t_1 \geq I\left(i-\left(\frac{p-1}{2}\right)+x, j-\left(\frac{p-1}{2}\right)+y\right) \text{ and } k_{i,j} \geq \Phi_1, \\ \Phi_0 & \text{otherwise,} \end{cases}$$

wherein $t_1$ and $t_2$ are respectively lower and upper intensity bounds for a healthy lumen, and for a mucus-filled airway, $$w_{x,y}^{ij} = \begin{cases} \Phi_2 & \text{if } t_2 \leq I\left(i-\left(\frac{p-1}{2}\right)+x, j-\left(\frac{p-1}{2}\right)+y\right) \text{ and } k_{i,j} \geq \Phi_2, \\ \Phi_1 & \text{if } d_{muc} \geq I\left(i-\left(\frac{p-1}{2}\right)+x, j-\left(\frac{p-1}{2}\right)+y\right) \text{ and } k_{i,j} \geq \Phi_1, \\ \Phi_0 & \text{otherwise,} \end{cases}$$

wherein $d_{muc}$ is a mucus minimum density.

12. The method of claim 11, wherein said correlation C between processed 2D cross section and said airway model is calculated as $$C^{ij} = \frac{\sum_{x=0}^{p-1}\sum_{y=0}^{p-1} w_{x,y}^{ij}}{\sum_{x=0}^{p-1}\sum_{y=0}^{p-1} k_{x,y}}$$

wherein $0 \leq C^{ij} \leq 1$, and wherein a correlation greater a predefined first tolerance value is indicative of a mucus plug and a correlation greater a predefined second tolerance value less than said first tolerance value is indicative of a clean airway.

13. A method for detecting and localizing mucus plugs in digitized lung images comprising the steps of:

providing a digitized lung image volume comprising a plurality of intensities corresponding to a 3-dimensional grid of points;

correlating a p×p airway model to an m×n 2D airway cross section I extracted from said lung image from $$C^{ij} = \frac{\sum_{x=0}^{p-1}\sum_{y=0}^{p-1} w_{x,y}^{ij}}{\sum_{x=0}^{p-1}\sum_{y=0}^{p-1} k_{x,y}},$$

wherein $0 \leq C^{ij} \leq 1$, $x, y \in \mathbb{Z}$, $x \in [0, \ldots, p-1]$ and $y \in [0, \ldots, p-1]$, $$k_{x,y} = \begin{cases} 2 & \text{if } h < \|(k_{x,y}, k_{p/2,p/2})\| \leq p/2, \\ 1 & \text{if } h \geq \|(k_{x,y}, k_{p/2,p/2})\|, \\ 0 & \text{otherwise,} \end{cases}$$

wherein h is a lumen diameter of said airway, and (p/2)−h is a wall thickness of said airway, wherein for a clean airway, $$w_{x,y}^{ij} = \begin{cases} 2 & \text{if } t_2 \leq I\left(i-\left(\frac{p-1}{2}\right)+x, j-\left(\frac{p-1}{2}\right)+y\right) \text{ and } k_{i,j} \geq 2, \\ 1 & \text{if } t_1 \geq I\left(i-\left(\frac{p-1}{2}\right)+x, j-\left(\frac{p-1}{2}\right)+y\right) \text{ and } k_{i,j} \geq 1, \\ 0 & \text{otherwise,} \end{cases}$$

wherein $t_1$ and $t_2$ are respectively lower and upper intensity bounds for a healthy lumen, wherein for a mucus-filled airway, $$w_{x,y}^{ij} = \begin{cases} 2 & \text{if } t_2 \leq I\left(i-\left(\frac{p-1}{2}\right)+x, j-\left(\frac{p-1}{2}\right)+y\right) \text{ and } k_{i,j} \geq 2, \\ 1 & \text{if } d_{muc} \geq I\left(i-\left(\frac{p-1}{2}\right)+x, j-\left(\frac{p-1}{2}\right)+y\right) \text{ and } k_{i,j} \geq 1, \\ 0 & \text{otherwise,} \end{cases}$$

wherein $d_{muc}$ is a mucus minimum density, and wherein a correlation greater a predefined high tolerance value is indicative of a mucus plug and a correlation greater a predefined low tolerance value less than said first tolerance value is indicative of a clean airway.

14. The method of claim 13, further comprising extracting a bronchial tree from said lung image, said bronchial tree comprising a plurality of branching airways terminating at terminal points; and computing a distance map along said bronchial tree to obtain a lumen diameter along the bronchial tree.

15. The method of claim 14, wherein extracting said m×n 2D airway cross section I comprises selecting an extended point beyond a terminal point of an airway branch in a direction of said airway branch; extracting said 2-dimensional cross section I of size m×n points from said lung image about said extended point.

16. The method of claim 13, further comprising forming a union of all local neighborhood functions $$\bigcup_{i,j} W^{ij}$$

for $i \in [0, \ldots, m-1]$ and $j \in [0, \ldots, n-1]$ wherein $$W^{ij}(x, y) = \begin{pmatrix} w_{0,0}^{ij} & \cdots & w_{0,p-1}^{ij} \\ \vdots & \ddots & \vdots \\ w_{p-1,0}^{ij} & \cdots & w_{p-1,p-1}^{ij} \end{pmatrix},$$

$$\forall i \in [0, \ldots, m-1], \forall j \in [0, \ldots, n-1].$$

17. A non-transitory program storage device readable by a computer, tangibly embodying a program of instructions executable by the computer to perform the method steps for detecting and localizing mucus plugs in digitized lung images, said method comprising the steps of:

providing a digitized lung image volume comprising a plurality of intensities corresponding to a 3-dimensional grid of points;

extracting a bronchial tree from said lung image, said bronchial tree comprising a plurality of branching airways terminating at terminal points;

providing a model of a 2-dimensional cross section of an airway;

selecting an extended point beyond a terminal point of an airway branch in a direction of said airway branch;

obtaining a 2-dimensional cross section I of size m×n points from said lung image about said selected point;

processing said 2D cross section I by calculating a local neighborhood function for each point in the cross section and forming a union of all local neighborhood functions; and calculating a correlation between processed 2D cross section and said airway model, wherein said correlation is indicative of the presence of a mucus plug within said airway.

18. The computer readable program storage device of claim 17, wherein extracting a bronchial tree from said lung image comprises segmenting said image volume using an adaptive threshold method and applying an iterative region-growing until terminal points of the airway branches are reached, and skeletonizing to obtain a bronchial tree structure comprising a set of branches, each branch comprising a set of ordered sites.

19. The computer readable program storage device of claim 17, the method further comprising computing a distance map along said bronchial tree to obtain a lumen diameter along the bronchial tree.

20. The computer readable program storage device of claim 19, wherein said airway model is a 2-dimensional p×p image template defined as $$K(x, y) = \begin{pmatrix} k_{0,0} & \cdots & k_{0,p-1} \\ \vdots & \ddots & \vdots \\ k_{p-1,0} & \cdots & k_{p-1,p-1} \end{pmatrix},$$

wherein $x, y \in Z$, $x \in [0, \ldots, p-1]$, and $y \in [0, \ldots, p-1]$, and wherein $$k_{x,y} = \begin{cases} \Phi_2 & \text{if } h < \|(k_{x,y}, k_{p/2,p/2})\| \le p/2, \\ \Phi_1 & \text{if } h \ge \|(k_{x,y}, k_{p/2,p/2})\|, \\ \Phi_0 & \text{otherwise,} \end{cases}$$

wherein $\Phi_0, \Phi_1, \Phi_2$ are distinct integers with $\Phi_0 < \Phi_1 < \Phi_2$, h is an airway lumen diameter, and (p/2)−h is an airway wall thickness.

21. The computer readable program storage device of claim 20, wherein $\Phi_0=0$, $\Phi_1=1$, and $\Phi_2=2$.

22. The computer readable program storage device of claim 20, wherein calculating the lumen diameter of said airway model for the airway branch of the extended point comprises selecting a portion of said airway branch, selecting a plurality of cross-sections along said branch portion, obtaining a lumen diameter for each cross section from said distance map, and calculating an average of each cross section lumen diameter.

23. The computer readable program storage device of claim 22, wherein calculating the wall thickness of said airway model for the airway branch comprises selecting a cross-section at a mid point of said branch portion, projecting a plurality of rays from a skeleton mid point of said cross section, finding a wall thickness from an intensity profile along each ray using a full-width-half-max criteria, and averaging the wall thickness of each ray.

24. The computer readable program storage device of claim 22, wherein the wall thickness is estimated as 1/(lumen diameter).

25. The computer readable program storage device of claim 23, the method further comprising estimating lower and upper intensity thresholds for healthy airways by selecting a cross section at the mid point of said branch, setting said lower intensity threshold $t_1$ to the maximum intensity of the lumen in said cross section, estimating the upper intensity threshold $t_2$ by averaging intensity values along said plurality of rays within an estimated wall thickness interval, and estimating a mucus Minimum density $d_{muc}$ as a maximum intensity value over said branch portion.

26. The computer readable program storage device of claim 23, the method further comprising estimating lower and upper intensity thresholds for healthy airways by setting said thresholds to pre-determined values, and estimating a mucus minimum density as being approximately equal to said lower threshold.

27. The computer readable program storage device of claim 20, wherein calculating a local neighborhood function for each point in the cross section comprises defining a local p-neighborhood $W^{ij}$ of each point (x, y) of said cross-section as $$W^{ij}(x, y) = \begin{pmatrix} w_{0,0}^{ij} & \cdots & w_{0,p-1}^{ij} \\ \vdots & \ddots & \vdots \\ w_{p-1,0}^{ij} & \cdots & w_{p-1,p-1}^{ij} \end{pmatrix},$$

$$\forall i \in [0, \ldots, m-1], \forall j \in [0, \ldots, n-1],$$

wherein said union of all local neighborhood functions is $$\bigcup_{i,j} W^{ij}$$

for $i \in [0, \ldots, m-1]$ and $j \in [0, \ldots, n-1]$, wherein, $\forall x \in [0, \ldots, p-1]$, $\forall y \in [0, \ldots, p-1]$, for a clean airway, $$w_{x,y}^{ij} = \begin{cases} \Phi_2 & \text{if } t_2 \le I\left(i-\left(\frac{p-1}{2}\right)+x, j-\left(\frac{p-1}{2}\right)+y\right) \text{ and } k_{i,j} \ge \Phi_2, \\ \Phi_1 & \text{if } t_1 \ge I\left(i-\left(\frac{p-1}{2}\right)+x, j-\left(\frac{p-1}{2}\right)+y\right) \text{ and } k_{i,j} \ge \Phi_1, \\ \Phi_0 & \text{otherwise,} \end{cases}$$

wherein $t_1$ and $t_2$ are respectively lower and upper intensity bounds for a healthy lumen, and for a mucus-filled airway, $$w_{x,y}^{ij} = \begin{cases} \Phi_2 & \text{if } t_2 \le I\left(i-\left(\frac{p-1}{2}\right)+x, j-\left(\frac{p-1}{2}\right)+y\right) \text{ and } k_{i,j} \ge \Phi_2, \\ \Phi_1 & \text{if } d_{muc} \ge I\left(i-\left(\frac{p-1}{2}\right)+x, j-\left(\frac{p-1}{2}\right)+y\right) \text{ and } k_{i,j} \ge \Phi_1, \\ \Phi_0 & \text{otherwise,} \end{cases}$$

wherein $d_{muc}$ is a mucus minimum density.

28. The computer readable program storage device of claim 27, wherein said correlation C between processed 2D cross section and said airway model is calculated as $$C^{ij} = \frac{\sum_{x=0}^{p-1} \sum_{y=0}^{p-1} w_{x,y}^{ij}}{\sum_{x=0}^{p-1} \sum_{y=0}^{p-1} k_{x,y}}$$

wherein $0 \leq C^{ij} < 1$, and wherein a correlation greater a predefined first tolerance value is indicative of a mucus plug and a correlation greater a predefined second tolerance value less than said first tolerance value is indicative of a clean airway.

* * * * *